United States Patent
Maruyama et al.

(10) Patent No.: US 6,639,111 B2
(45) Date of Patent: Oct. 28, 2003

(54) 5-THIA-ω-(SUBSTITUTED PHENYL)-PROSTAGLANDIN E ALCOHOLS, PROCESS FOR PREPARING THE ALCOHOLS AND PHARMACEUTICAL PREPARATIONS CONTAINING THE SAME AS THE ACTIVE INGREDIENT

(75) Inventors: Toru Maruyama, Mishima-gun (JP); Kaoru Kobayashi, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/169,602

(22) PCT Filed: Dec. 27, 2000

(86) PCT No.: PCT/JP00/09308

§ 371 (c)(1),
(2), (4) Date: Jul. 3, 2002

(87) PCT Pub. No.: WO01/49661

PCT Pub. Date: Jul. 12, 2001

(65) Prior Publication Data

US 2003/0097023 A1 May 22, 2003

(30) Foreign Application Priority Data

Jan. 5, 2000 (JP) .......................................... 2000-000416

(51) Int. Cl.[7] .......................... C07C 321/00; A61K 31/10
(52) U.S. Cl. ............................ 568/46; 568/45; 514/706
(58) Field of Search .......................... 514/706; 568/38, 568/39, 45, 46

(56) References Cited

U.S. PATENT DOCUMENTS

| | | | |
|---|---|---|---|
| 4,175,201 A | * 11/1979 | Fried | ........................... 560/17 |
| 4,271,314 A | 6/1981 | Collins et al. | |
| 4,529,812 A | 7/1985 | Collins et al. | |
| 5,599,838 A | * 2/1997 | Sato et al. | ................... 514/530 |
| 6,172,109 B1 | * 1/2001 | Zinke et al. | ................ 514/530 |
| 6,262,293 B1 | * 7/2001 | Tani et al. | ..................... 560/18 |
| 6,462,081 B1 | * 10/2002 | Maruyama et al. | ......... 514/530 |

OTHER PUBLICATIONS

CA:134:290416 abs of WO 2001024800 Apr. 12, 2001.*

* cited by examiner

Primary Examiner—Jean F. Vollano
(74) Attorney, Agent, or Firm—Sughrue Mion, PLLC

(57) ABSTRACT

A 5-thia-ω-substituted phenyl-prostaglandin E alcohol of the formula (I)

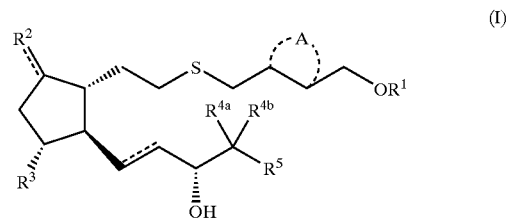

(I)

(wherein, all the symbols are the same meanings as defined in the specification), a process for producing it and a pharmaceutical composition comprising it as an active ingredient.

The compounds of the formula (I) may be converted into carboxylic acids in the living body which can bind on $PGE_2$ receptors (especially, subtype $EP_4$) strongly, so the compounds of the formula (I) are expected to be useful for prevention and/or treatment of immunological diseases, asthma, abnormal bone formation, neuronal cell death, lung failure, liver damage, acute hepatitis, nephritis, renal insufficiency, hypertension, myocardial ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, shock, sleeping disorder and blood platelet aggregation.

12 Claims, No Drawings

5-THIA-ω-(SUBSTITUTED PHENYL)-PROSTAGLANDIN E ALCOHOLS, PROCESS FOR PREPARING THE ALCOHOLS AND PHARMACEUTICAL PREPARATIONS CONTAINING THE SAME AS THE ACTIVE INGREDIENT

FIELD OF THE INVENTION

The present invention relates to a 5-thia-ω-substituted phenyl-prostaglandin E alcohol.

More detail, it relates to a 5-thia-ω-substituted phenyl-prostaglandin E alcohol of the formula (I)

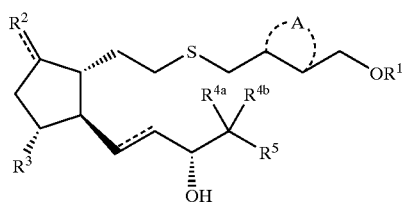

(wherein, all the symbols are the same meaning as defined hereinafter), a process for producing it and a pharmaceutical composition it as an active ingredient.

BACKGROUND

Prostaglandin $E_2$ (abbreviated as $PGE_2$) has been known as a metabolite in the arachidonate cascade. It has been known that $PGE_2$ possesses cyto-protective activity, uterine contractile activity, a pain-inducing effect, a promoting effect on digestive peristalsis, an awakening effect, a suppressive effect on gastric acid secretion, hypotensive activity and diuretic activity etc.

A recent study has proved existence of various $PGE_2$ subtype receptors possessing a different physical role from each other. At present, four receptor subtypes are known and they are called $EP_1$, $EP_2$, $EP_3$, $EP_4$ (Negishi M. et al, J. Lipid Mediators Cell Signaling, 12, 379–391 (1995)).

It is thought that $EP_4$ subtype receptor relates to inhibition of producing TNF-α and acceleration of producing IL-10. Therefore, the compounds which can bind on $EP_4$ subtype receptor strongly are expected to be useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus etc., and rejection after organ transplantation etc.), asthma, abnormal bone formation, neuronal cell death, lung failure, liver damage, acute hepatitis, nephritis, renal insufficiency, hypertension, myocardiac ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc. Further, it is thought that $EP_4$ subtype receptor relates to sleeping disorder and blood platelet aggregation, so such compounds are expected to be useful for the prevention and/or treatment of these diseases.

The present inventors et al. have found out that 5-thia-prostaglandin derivatives of the following formula (A) are useful as a compound which satisfies these purposes and have filed a patent application relates to such compounds (WO00/03980). These compounds can bind on $EP_4$ subtype receptor selectively and binds on the other subtype receptors weakly, so they show no any other activities. Therefore they are expected to be drugs possessing less side effects. 5-Thia-ω-substituted phenyl-prostaglandin E derivatives of the following formula (A):

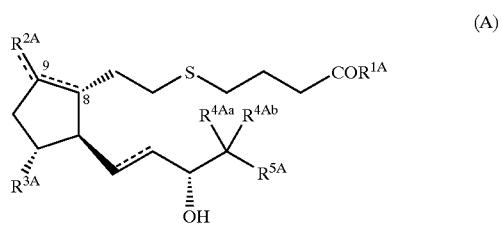

(wherein, $R^{1A}$ is hydroxy, C1–6 alkyloxy, or the formula: $NR^{6A}R^{7A}$ (in which, $R^{6A}$ and $R^{7A}$ are, independently, hydrogen or C1–4 alkyl), $R^2$ is oxo, halogen or the formula: O—$COR^{8A}$ (in which, $R^{8A}$ is C1–4 alkyl, phenyl or phenyl(C1–4 alkyl)), $R^{3A}$ is hydrogen or hydroxy, $R^{4Aa}$ and $R^{4Ab}$ are, independently, hydrogen or C1–4 alkyl, $R^{5A}$ is phenyl substituted with the following group:
 i) 1–3 of substituent(s) selected from the group consisting of
  C1–4 alkyloxy-C1–4 alkyl,
  C2–4 alkenyloxy-C1–4 alkyl,
  C2–4 alkynyloxy-C1–4 alkyl,
  C3–7 cycloalkyloxy-C1–4 alkyl,
  C3–7 cycloalkyl(C1–4 alkyloxy)-C1–4 alkyl,
  phenyloxy-C1–4 alkyl,
  phenyl-C1–4 alkyloxy-C1–4 alkyl,
  C1–4 alkylthio-C1–4 alkyl,
  C2–4 alkenylthio-C1–4 alkyl,
  C2–4 alkynylthio-C1–4 alkyl,
  C3–7 cycloalkylthio-C1–4 alkyl,
  C3–7 cycloalkyl(Cl-4 alkylthio)-C1–4 alkyl,
  phenylthio-C1–4 alkyl, or
  phenyl-C1–4 alkylthio-C1–4 alkyl,
 ii) C1–4 alkyloxy-C1–4 alkyl and C1–4 alkyl,
  C1–4 alkyloxy-C1–4 alkyl and C1–4 alkyloxy,
  C1–4 alkyloxy-C1–4 alkyl and hydroxy,
  C1–4 alkyloxy-C1–4 alkyl and halogen,
  C1–4 alkylthio-C1–4 alkyl and C1–4 alkyl,
  C1–4 alkylthio-C1–4 alkyl and C1–4 alkyloxy,
  C1–4 alkylthio-C1–4 alkyl and hydroxy, or
  C1–4 alkylthio-C1–4 alkyl and halogen,
 iii) haloalkyl or hydroxy-C1–4 alkyl, or
 iv) C1–4 alkyl and hydroxy;
  ==== is a single bond or a double bond,
with the proviso that when $R^{2A}$ is the formula: O—$COR^{8A}$, bond of C8–C9 is a double bond) and cyclodextrin clathrate thereof are described in the specification of WO00/03980.

DISCLOSURE OF THE INVENTION

The present inventors et al. have studied to find out the stable compounds which can bind on $EP_4$ subtype receptor specifically, and do not bind on any other EP subtype receptors nor any other prostanoid receptors. The present inventors have found out 5-thiaprostaglandin wherein a substituted phenyl is introduced into ω-chain have achieved this object, and then filed the said patent application (WO00/03980).

The present inventors et al. have confirmed that converting carboxy group of the compounds described in the said patent application into hydroxy group (alcohol) improved an absorption of the compounds into the living body and then, have completed the present invention. The compounds of the formula (I) of the present invention may be converted into carboxylic acid which is an active compound by oxidation in the living body. The said active carboxylic acid possesses an activity to bind on $EP_4$ subtype receptor strongly and bind on the other prostanoid receptors including the other subtype receptors weakly, and a sufficient stability as a drug.

That is to say, the present invention relates to (1) a 5-thia-ω-substituted phenyl-prostaglandin E alcohol of the formula (I)

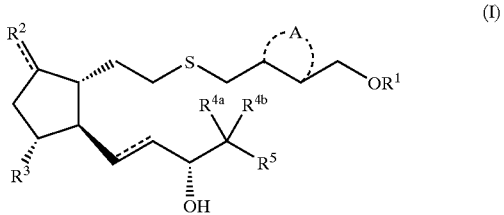

(wherein, —A— is absent or —A— is methylene or ethylene, $R^1$ is hydrogen, C1–6 alkyl, phenyl-C1–6 alkyl, C2–6 alkanoyl, or phenyl-C2–6 alkanoyl, $R^2$ is oxo or halogen, $R^3$ is hydrogen or hydroxy, $R^{4a}$ and $R^{4b}$ are, independently, hydrogen or C1–4 alkyl, $R^5$ is phenyl substituted with the following group:
  i) 1–3 of group selected from the group consisting of
   C1–4 alkyloxy-C1–4 alkyl,
   C2–4 alkenyloxy-C1–4 alkyl,
   C2–4 alkynyloxy-C1–4 alkyl,
   C3–7 cycloalkyloxy-C1–4 alkyl,
   C3–7 cycloalkyl(C1–4 alkyloxy)-C1–4 alkyl,
   phenyloxy-C1–4 alkyl,
   phenyl-C1–4 alkyloxy-C1–4 alkyl,
   C1–4 alkylthio-C1–4 alkyl,
   C2–4 alkenylthio-C1–4 alkyl,
   C2–4 alkynylthio-C1–4 alkyl,
   C3–7 cycloalkylthio-C1–4 alkyl,
   C3–7 cycloalkyl(C1–4 alkylthio-)-C1–4 alkyl,
   phenylthio-C1–4 alkyl, and
   phenyl-C1–4 alkylthio-C1–4 alkyl,
  ii) C1–4 alkyloxy-C1–4 alkyl and C1–4 alkyl,
   C1–4 alkyloxy-C1–4 alkyl and C1–4 alkyloxy,
   C1–4 alkyloxy-C1–4 alkyl and hydroxy,
   C1–4 alkyloxy-C1–4 alkyl and halogen,
   C1–4 alkylthio-C1–4 alkyl and C1–4 alkyl,
   C1–4 alkylthio-C1–4 alkyl and C1–4 alkyloxy,
   C1–4 alkylthio-C1–4 alkyl and hydroxy, or
   C1–4 alkylthio-C1–4 alkyl and halogen,
  iii) haloalkyl or hydroxy-C1–4 alkyl, or
  iv) C1–4 alkyl and hydroxy;
   ==== is a single bond or a double bond) or cyclodextrin clathrate thereof, (2) a process for producing it and (3) a pharmaceutical composition comprising it as an active ingredient.

In the formula (I), C1–4 alkyl in $R^{4a}$, $R^{4b}$ and $R^5$ means methyl, ethyl, propyl, butyl and isomers thereof.

In the formula (I), C1–6 alkyl in $R^1$ means methyl, ethyl, propyl, butyl, pentyl, hexyl and isomers thereof.

In the formula (I), C2–6 alkyl in $R^1$ means ethyl, propyl, butyl, pentyl, hexyl and isomers thereof.

In the formula (I), C2–6 alkanoyl in $R^1$ means acetyl, propanoyl, butanoyl, pentanoyl, hexanoyl and isomers thereof.

In the formula (I), C2–4 alkenyl in $R^5$ means vinyl, propenyl, butenyl and isomers thereof.

In the formula (I), C2–4 alkynyl in $R^5$ means ethynyl, propynyl, butynyl and isomers thereof.

In the formula (I), C3–7 cycloalkyl in $R^5$ means cyclopropyl, cyclobutyl, cyclopentyl, cyclohexyl, cycloheptyl.

In the formula (I), halogen in $R^2$ and $R^5$ means fluorine, chlorine, bromine and iodine.

In the present invention, the symbol ⦵ means single bond or double bond. Further, unless otherwise specified, in the present invention, the symbol ⦵ means that the substituent attached thereto is in front of the sheet, the symbol ⦵ means that the substituent attached thereto is behind the sheet and the symbol ⦵ means that there is a mixture of substituents in front of and behind the sheet or that the substituent attached thereto may be in front of or behind the sheet as would be clear to the person skilled in the art.

Unless otherwise specified, all isomers are included in the present invention. For example, alkyl, alkenyl, alkynyl, alkylene group means straight-chain or branched-chain ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

In the formula (I), the substituent(s) of phenyl in $R^5$ is preferably substituted at 3-position, 3-position and 4-position, and 3-position and 5-position.

In the formula (I), each group (i) to (iv) as the substituent (s) of phenyl in $R^5$ means as follows:
   group i) means 1, 2 or 3 of alkyloxyalkyl etc.,
   group ii) means at least one alkyloxyalkyl etc. and at least one alkyl, alkyloxy, hydroxy or halogen,
   group iii) means alkyl substituted with 1 or 2 of halogen or hydroxy and group iv) means at least one alkyl and at least one hydroxy.

Among the compounds of the present invention of the formula (I), the compounds described in the Examples, the compounds shown in the following Tables are preferable.

TABLE 1
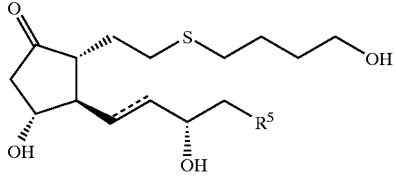
R⁵
| | | |
|---|---|---|
| 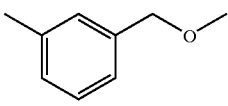 | 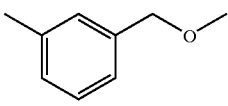 | 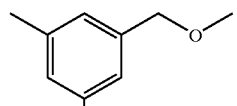 |
| 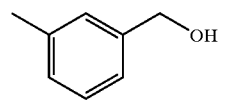 | 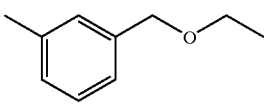 | 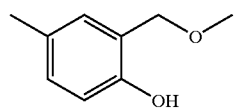 |
| 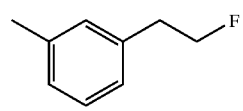 | 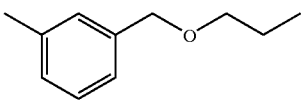 | 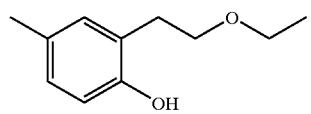 |
| 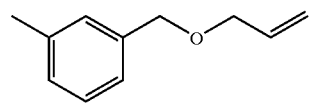 | 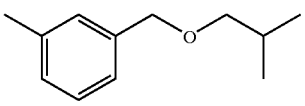 | 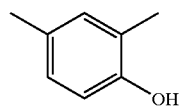 |
| 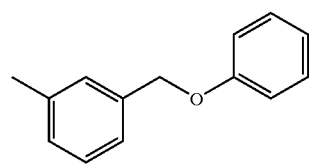 | 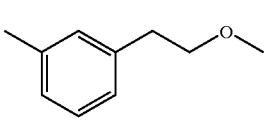 | |
| 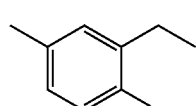 | 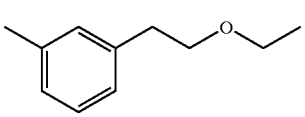 | |
| 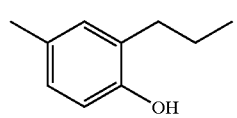 | | |
| 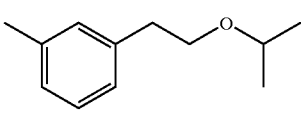 | | |

TABLE 2
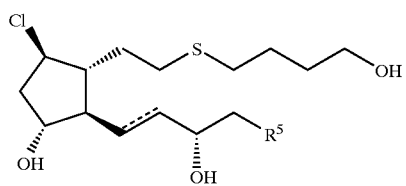
(2)
R⁵

TABLE 3
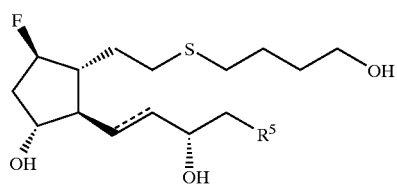
(3)
R⁵

TABLE 4
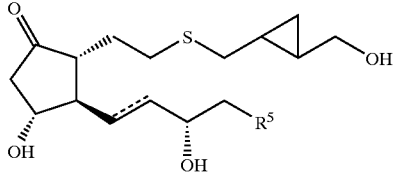
(4)
R⁵
| | | |
|---|---|---|
|  | 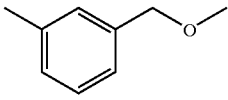 | 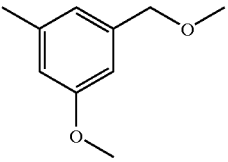 |
| 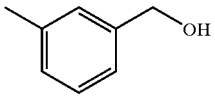 | 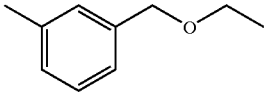 | 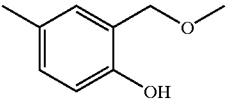 |
| 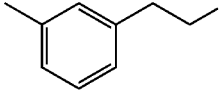 | 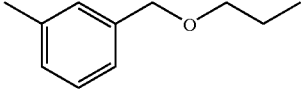 | 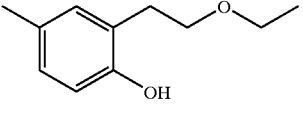 |
| 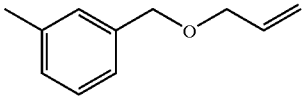 | 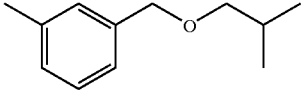 | 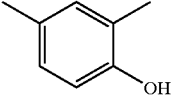 |
| 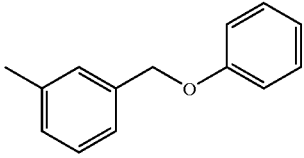 | 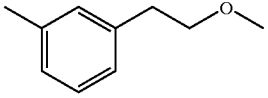 | |
| 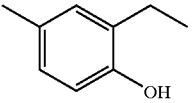 | 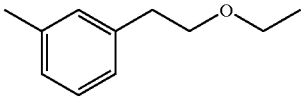 | |
| 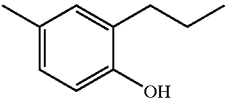 | | |
| 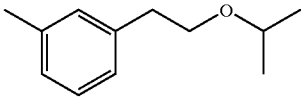 | | |

TABLE 5

(5)

[Structure: cyclopentane core with Cl, S-CH2-cyclopropyl-CH2OH substituent, OH groups, and R5 side chain via vinyl-CHOH-CH2-R5]

| R5 |
|---|

| | | |
|---|---|---|
| 3-methylbenzyl methyl ether | 3,5-disubstituted benzyl methyl ether with methoxy | 3-methylbenzyl alcohol |
| 3-methylbenzyl ethyl ether | 2-(methoxymethyl)-4-methylphenol | 1-(2-fluoroethyl)-3-methylbenzene |
| 3-methylbenzyl propyl ether | 2-(2-ethoxyethyl)-4-methylphenol | 3-methylbenzyl allyl ether |
| 3-methylbenzyl isobutyl ether | 2,4-dimethylphenol | 3-methylbenzyl phenyl ether |
| 1-methyl-3-(2-methoxyethyl)benzene | 2-ethyl-4-methylphenol | |
| 1-methyl-3-(2-ethoxyethyl)benzene | 4-methyl-2-propylphenol | |
| 1-methyl-3-(2-isopropoxyethyl)benzene | | |
| 1-methyl-3-(2-propoxyethyl)benzene | | |

TABLE 6

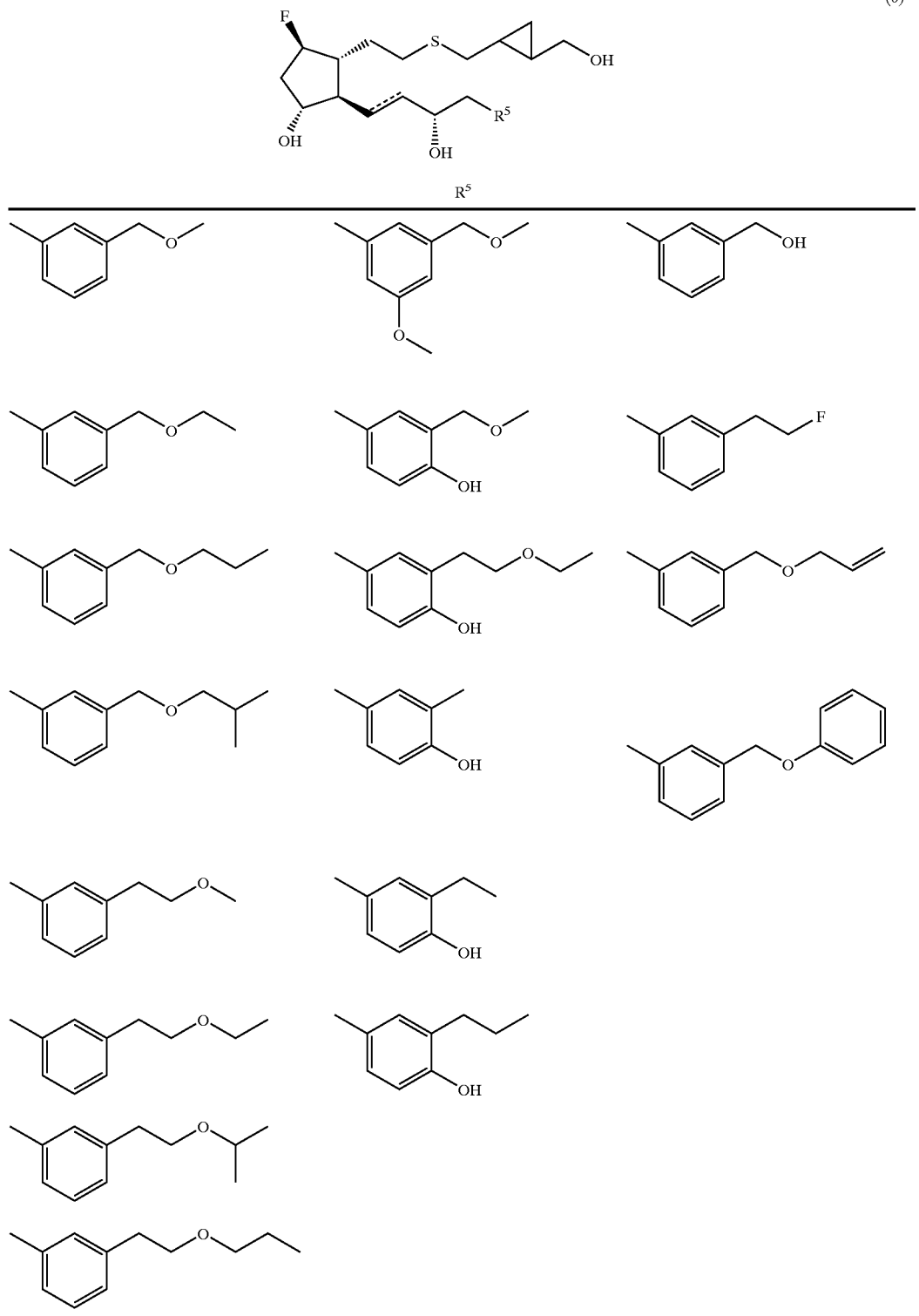

Cyclodextrin Clathrate

The compounds of the present invention of the formula (I) may be converted into the corresponding cyclodextrin clathrates by the method described in the specification of Japanese Patent Application Kokoku Sho 50-3362, 52-31404 or 61-52146 using α-, β- or γ-cyclodextrin or a mixture thereof. Converting into the corresponding cyclodextrin clathrates serves to increase the stability and solubility in water of the compounds, and therefore it is useful in the use for pharmaceuticals.

Process for Producing the Compounds of the Present Invention

The compounds of the formula (I)

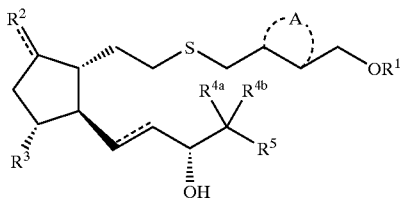

(wherein, all the symbols are the same meaning as defined hereinbefore) may be prepared from the compounds of the formula (II)

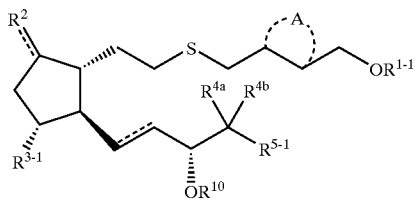

(wherein, $R^{1-1}$ is C1–6 alkyl, phenyl-C1–6 alkyl, C2–6 alkanoyl, phenyl-C2–6 alkanoyl, or a protecting group of hydroxy which is removed under an acidic condition, $R^{3-1}$ is hydrogen or hydroxy group protected by a protecting group of hydroxy which is removed under an acidic condition, $R^{10}$ is a protecting group of hydroxy which is removed under an acidic condition, $R^{5-1}$ is the same meaning of $R^5$ provided that hydroxy group in the group represented by $R^{5-1}$ is protected by a protecting group which is removed under an acidic condition, and the other symbols are the same meaning as defined hereinbefore) by reaction for removal of a protecting group under an acidic condition.

A protecting group of hydroxy which is removed under an acidic condition includes, for example, t-butyldimethylsilyl, triphenylmethyl, and tetrahydropyran-2-yl (THP) etc.

Hydrolysis under an acidic condition has been known. This reaction may be carried out, for example, in an organic solvent which is admissible with water (e.g., tetrahydrofran, methanol, ethanol, dimethoxyethane, acetonitrile or mixture thereof etc.), using an inorganic acid (e.g., hydrochloric acid, phosphoric acid, hydrofluoric acid, hydrogen fluoride-pyridine etc.) or an organic acid (e.g., acetic acid, tosylic acid, trichloroacetic acid etc.) at temperature of 0–50° C.

The compounds of the formula (II) may be prepared by the following Reaction Schemes 1–3.

Each symbol in Reaction Schemes means as follows or same meaning defined hereinbefore:

Ms: methanesulfony,
Ts: p-toluenesulfonyl,
$R^{2-1}$: halogen,
Ac: acetyl,
TMS: trimethylsilyl.

Reaction Scheme 1

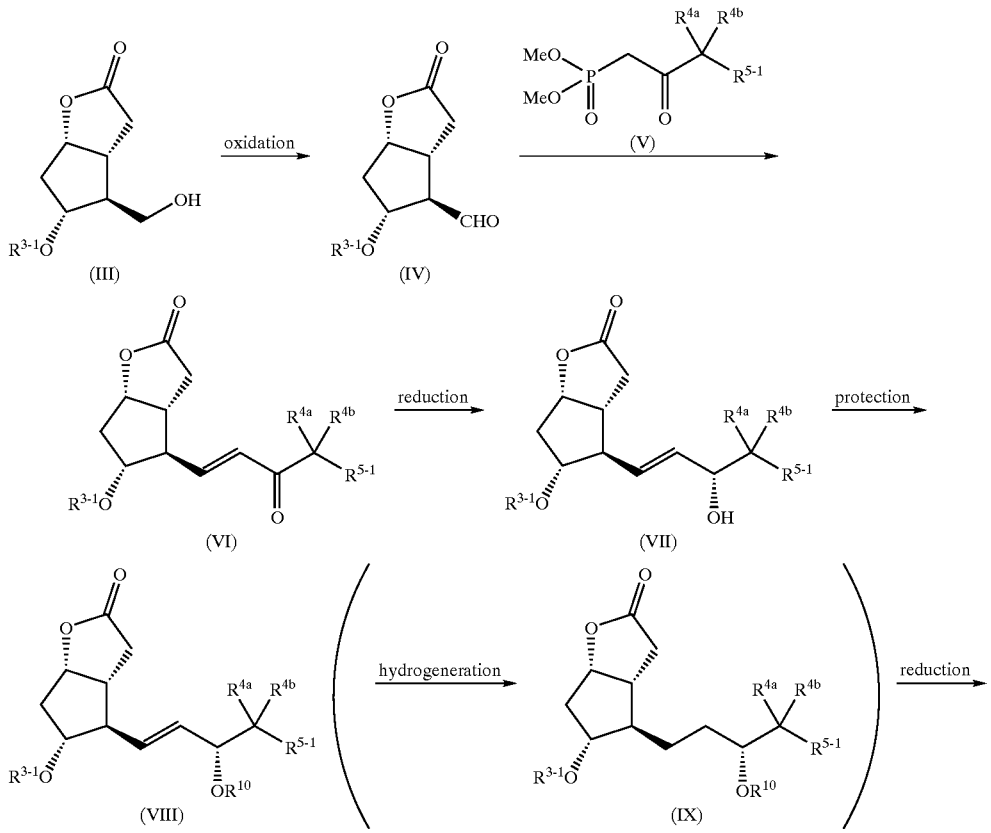

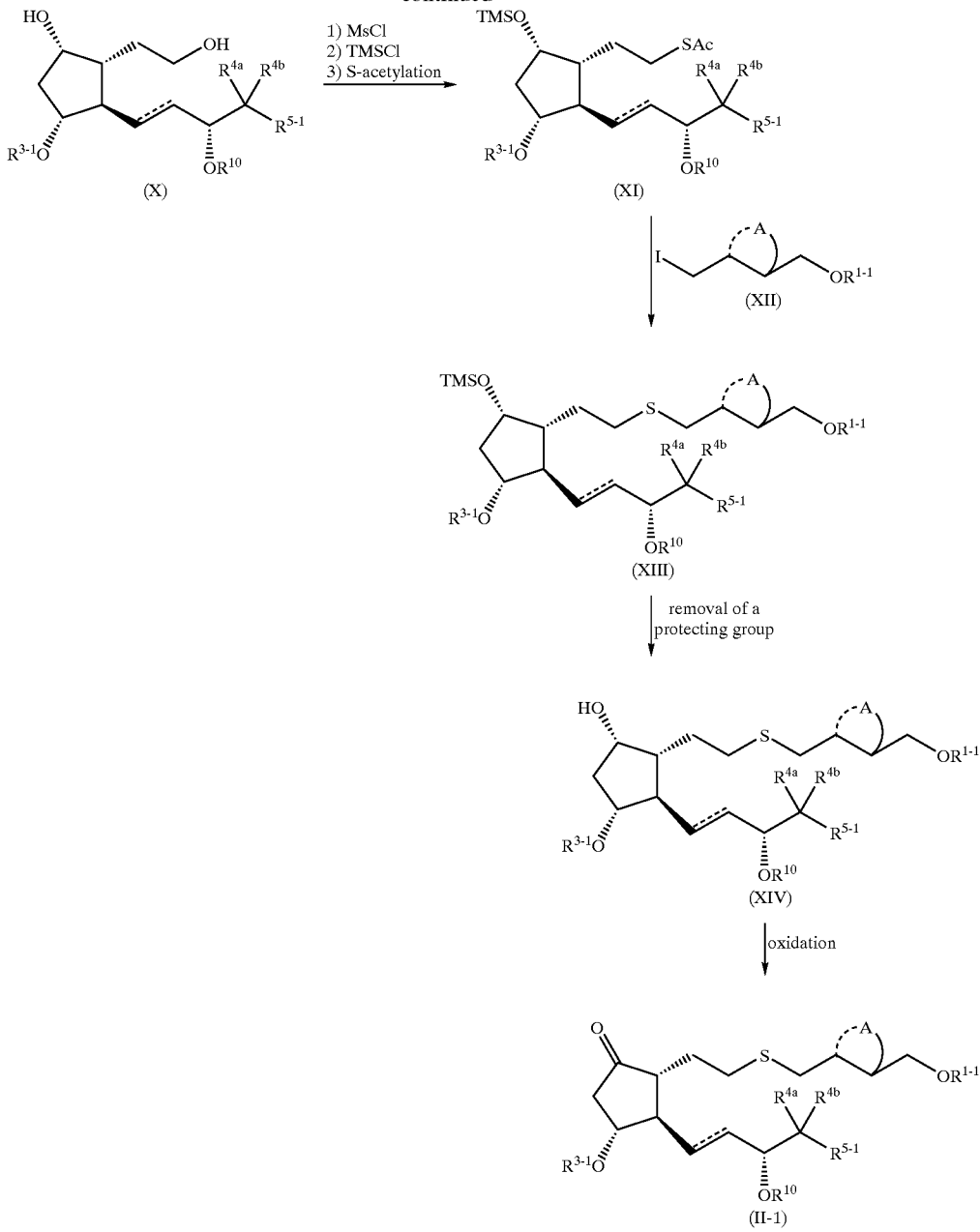
Reaction Scheme 2
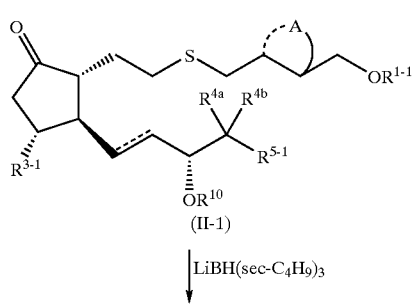
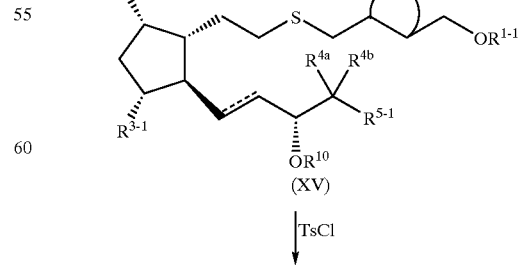

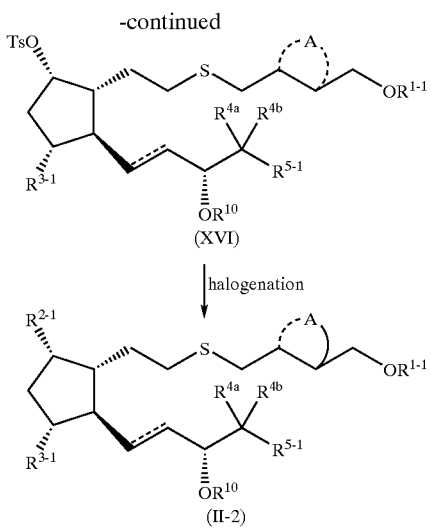

Starting Materials and Reagents

Each Reaction in the said Reaction Schemes may be carried out by known methods. In the said Reaction Schemes, the compounds of the formulae (III), (V) and (XII) as starting materials have been known or may be prepared easily by known methods.

For example, the compounds of the formula (III) wherein $R^{3-1}$ is THP have been described in J. Am. Chem. Soc., 98, 1490 (1971).

The other starting materials and reagents in the present invention are known per se or may be prepared by known methods.

In each reaction in the present specification, reaction products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

Pharmacological Activities

The compounds of the present invention of the formula (I) may be converted into carboxylic acids by oxidation in the living body. As described in the specification of WO00/03980, the corresponding carboxylic acids can bind strongly on $EP_4$ subtype receptor which is one of $PGE_2$ receptors and show an activity on it.

For example, in the laboratory experiments, the inhibitory action on producing TNF-α induced by lipopolysaccharide (LPS) or the conversion of the compounds of the present invention into carboxylic acids in the living body has been confirmed by assaying the concentration in the blood plasma of rat.

Inhibitory Action on Producing TNF-α

LPS (10 μg/2 ml/kg) was administered into a tail vein of SD-strain male rat. Blood was collected from an abdominal large vein with heparin after 90 minutes from administration to prepare blood plasma. The amount of TNF-α in the blood plasma was determined by using ELISA Kit (Rat TNF-α Immunoassay kit, Biosource Co.). Each compound of the present invention was administered orally before 30 minutes from administration of LPS. The effective dose (IC50) was defined as the dose at which the test compound showed 50% inhibition on producing TNF-α in blood plasma, when the amount of producing TNF-α in the control group (administration of LPS, non-administration of test compound) was as 100%. The results are shown in Table 4.

TABLE 4

| Example No | Effective dose IC50 ($\mu$g/kg) p.o. |
|---|---|
| 1 | 117 |
| 1(1) | 57.4 |

Converting into Carboxylic Acid in the Living Body

The compound of Example 1(1) (1 mg/kg; alcohol compound) was administered into SD-strain male rat by intravenous route to determine each concentration of the said compound and corresponding carboxylic acid, i.e., (11$\alpha$, 15$\alpha$, 13E)-9-oxo-11,15-dihydroxy-16-(3-methoxymethylphenyl)-17,18,19,20-tetranor-5-thiaprost-13-enoic acid (corresponding carboxylic acid) in blood plasma. The test solution may be prepared from a physiological saline solution containing 0.3%ethanol and 0.1% POLYSORBATE 80. The concentration was determined by using liquid chromatograph mass spectrometer (LC/MS/MS). The results are shown in Table 5.

TABLE 5

| Compounds | Concentration in blood plasma $AUC_{0-\infty}$ (ng · hr/ml) |
|---|---|
| Example 1(1) | 462 ± 78 |
| corresponding carboxylic acid | 99 ± 26 |

Discussion

It has been confirmed that the alcohol compounds which were administered into living body were converted into carboxylic acids in it by oxidation.

Toxicity

The toxicity of the compounds of the formula (I) of the present invention is very low and therefore, it is confirmed that these compounds are safe for use as medicine.

Industrial Application
[Application for Pharmaceuticals]

The compounds of the present invention of the formula (I) may be converted into carboxylic acids by oxidation in the living body. Such carboxylic acids can bind on $PGE_2$ receptor and show the activity on it. Particularly, they bind on $EP_4$ subtype receptor strongly, so the compounds of the formula (I) are expected to be useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus etc., and rejection after organ transplantation etc.), asthma, abnormal bone formation, neuronal cell death, lung failure, liver damage, acute hepatitis, nephritis, renal insufficiency, hypertension, myocardiac ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc. Further, it is thought that $EP_4$ subtype receptor relates to sleeping disorder and blood platelet aggregation, so the compounds of the present invention are also expected to be useful for the prevention and/or treatment of such diseases.

The carboxylic acids converted from the compounds of the present invention of the formula (I) by oxidation might bind weakly on the subtypes receptors other than $EP_4$ subtype receptor do not express other effects, therefore such compounds are expected to be an agent having less side effect.

For the purpose above described, the compounds of the formula (I) of the present invention or cyclodextrin clathrate thereof may be normally administered systematically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 $\mu$g and 100 mg, by oral administration, up to several times per day, and between 0.1 $\mu$g and 10 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as solid compositions, liquid compositions or other compositions for oral administration, or as injections, liniments or suppositories etc. for parenteral administration.

Solid compositions for oral administration include compressed tablets, pills, capsules, dispersible powders, and granules etc.

Capsules contain hard capsules and soft capsules.

In such compositions, one or more of the active compound(s) is or are, admixed with at least one inert diluent such as lactose, mannitol, mannit, glucose, hydroxypropyl cellulose, microcrystalline cellulose, starch, polyvinylpyrrolidone, magnesium metasilicate aluminate.

The compositions may also comprise, as is normal practice, additional substances other than inert diluents: e.g. lubricating agents such as magnesium stearate, disintegrating agents such as cellulose calcium glycolate, and assisting agents for dissolving such as glutamic acid, asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2868691 or U.S. Pat. No. 3095355 may be used.

Injections for parenteral administration include sterile aqueous or non-aqueous solutions, suspensions and emul-

REFERENCE EXAMPLE 1

(9α, 15α, 13E)-1-t-Butyldimethylsilyloxy-9-hydroxy-15-(2-tetrahydropyranyloxy)-16-(3-methoxymethylphenyl)-17,18,19,20-tetranor-5-thiaprost-13-en

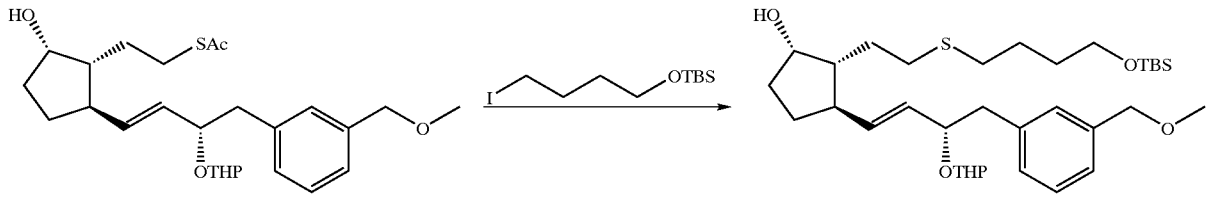

(9α, 11α, 15α, 13E)-6-Acetylthio-9-trimethylsilyloxy-15-(2-tetrahydropyranyloxy)-16-(3-methoxymethylphenyl)-1,2,3,4,5,17,18,19,20-nonanorprost-13-en (280 mg; prepared by the same procedure described in Reference Example 27 in the specification of WO00/03980) and 1-t-butyldimethylsilyloxy-4-iodobutane (345 mg) were dissolved into methanol. Thereto, potassium carbonate (152 mg) was added. The mixture was stirred for 2 hours at room temperature. After termination of reaction, ether was added to reaction solution. The mixture was washed by water and a saturated saline solution, dried over by anhydrous magnesium sulfate and concentrated under reduced pressure. The residue was purified with silica gel chromatography (hexane:ethyl acetate=4:1) to obtain the title compound (139 mg) having the following physical data.

TLC: Rf 0.52 (hexane:ethyl acetate=2:1); NMR(CDCl$_3$): δ 7.3–7.1 (m, 4H), 5.55–5.2 (m, 2H), 4.75–4.45 (m, 1H), 4.42 (s, 2H), 4.3–4.2 (m, 2H), 3.62 (t, J=5 Hz, 2H), 3.38 (s, 3H), 3.4–3.2 (m, 2H), 3.0–2.7 (m, 2H), 2.6–2.4 (m, 4H), 2.4–2.2 (m, 1H), 2.05–1.85 (m, 2H), 1.85–1.3 (m, 15H), 0.89 (s, 9H), 0.05 (s, 6H).

REFERENCE EXAMPLE 2

(15α, 13E)-1-t-Butyldimethylsilyloxy-9-oxo-15-(2-tetrahydropyranyloxy)-16-(3-methoxymethylphenyl)-17,18,19,20-tetranor-5-thiaprost-13-en

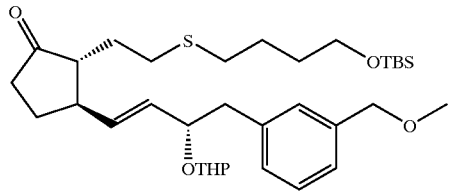

To a solution of (9α, 15α, 13E)-1-t-butyldimethylsilyloxy-9-hydroxy-15-(2-tetrahydropyranyloxy)-16-(3-methoxymethylphenyl)-17,18,19,20-tetranor-5-thiaprost-13-en (139 mg; prepared in Reference Example 1) in ethyl acetate (1.0 ml), isopropyldiethylamine (0.24 ml) was added. The mixture was cooled with ice. A solution of sulfur trioxide-pyridine complex (110 mg) in dimethylsulphoxide (DMSO; 1 ml) was added at a dropwise thereto for 1 minute. After stirring the mixture for 20 minutes, water was added thereto. The mixture was extracted with ethyl acetate. The organic layer was washed by 1N hydrochloric acid, water, a saturated solution of sodium hydrogen carbonate, a saturated saline solution, succeedingly, dried over by magnesium sulfate, and concentrated under reduced pressure to obtain the title compound having the following physical data. TLC: Rf 0.63 (hexane:ethyl acetate=2:1).

EXAMPLE 1

(15α, 13E)-9-oxo-15-Hydroxy-16-(3-methoxymethylphenyl)-17,18,19,20-tetranor-5-thiaprost-13-en-1-alcohol

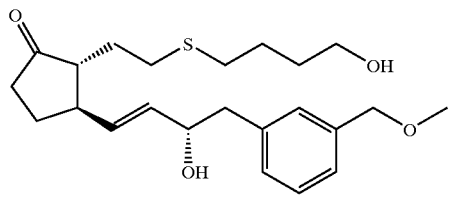

To a mixture solvent of acetonitlile (2 ml) and methanol (1 ml), (15α, 13E)-1-t-butyldimethylsilyloxy-9-oxo-15-(2-tetrahydropyranyloxy)-16-(3-methoxymethylphenyl)-17,18,19,20-tetranor-5-thiaprost-13-en (prepared in Reference Example 2) was dissolved. Thereto, 0.1N hydrochloric acid (1 ml) was added. The mixture was stirred for 2 hours at 35° C. After termination of reaction, a saturated solution of sodium hydrogen carbonate was added thereto. The mixture was extracted with ethyl acetate two times, washed by a saturated saline solution, dried over by magnesium sulfate and concentrated under reduced pressure. The residue was purified with silica gel chromatography (hexane:ethyl acetate=1:2 to 1:3) to obtain the title compound (72 mg) having the following physical data.

TLC: Rf 0.25 (ethyl acetate:hexane=2:1); NMR(CDCl$_3$): δ 7.3–7.1 (m, 4H), 5.75–5.6 (m, 2H), 4.44 (s, 2H), 4.4–4.3 (m, 1H), 3.65 (t, J=6 Hz, 2H), 3.41 (s, 3H), 2.9–2.7 (m, 2H), 2.7–2.3 (m, 6H), 2.3–2.0 (m, 3H), 2.0–1.5 (m, 9H).

EXAMPLES 1(1)–1(4)

By the same procedure as described in Reference Examples 1 and 2 and Example 1, the compounds having the following physical data were obtained.

EXAMPLE 1(1)

(11α, 15α, 13E)-9-oxo-11,15-Dihydroxy-16-(3-methoxymethylphenyl)-17,18,19,20-tetranor-5-thiaprost-13-en-1-alcohol

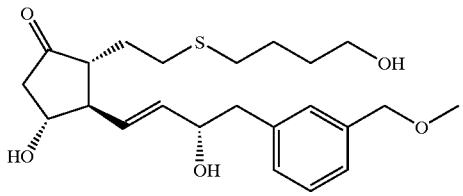

TLC: Rf 0.18 (ethyl acetate); NMR(CDCl$_3$): δ 7.35–7.17 (m, 4H), 5.77 (dd, J=15.0, 6.0 Hz, 1H), 5.54 (dd, J=15.0, 8.0 Hz, 1H), 4.48–4.38 (m, 3H), 4.00–3.90 (m, 1H), 3.68–3.63 (m, 2H), 3.42 (s, 3H), 3.01–2.21 (m, 11H), 1.92–1.55 (m, 8H).

EXAMPLE 1(2)

(11α, 15α, 13E)-9-oxo-11,15-Dihydroxy-16-methyl-16-(3-methyl-4-hydroxyphenyl)-17,18,19,20-tetranor-5-thiaprost-13-en-1-alcohol

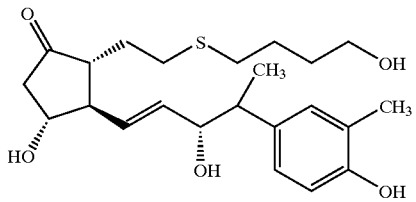

TLC: Rf 0.19 (ethyl acetate:methanol=50:1); NMR (CDCl$_3$): δ 7.0–6.7 (m, 3H), 5.68 and 5.53 (dd, J=15, 8 Hz, 1H), 5.57 and 5.35 (dd, J=15, 9 Hz, 1H), 4.2–3.9 (m, 2H), 3.65–3.6 (br, 2H), 2.8–2.0 (m, 16H), 2.0–1.5 (m, 6H), 1.32 and 1.20 (d, J=7 Hz, 3H).

EXAMPLE 1(3)

(11α, 15α, 13E)-9-oxo-11,15-Dihydroxy-16-methyl-16-(3-methoxymethylphenyl)-17,18,19,20-tetranor-5-thiaprost-13-en-1-alcohol

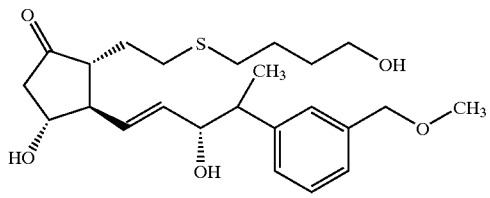

TLC: Rf 0.08 (ethyl acetate); NMR(CDCl$_3$): δ 7.36–7.10 (m, 4H), 5.71 (dd, J=15.3, 6.6 Hz, 0.5H), 5.62 (dd, J=15.6, 5.7 Hz, 0.5H), 5.53 (dd, J=16.0, 8.1 Hz, 0.5H), 5.47 (dd, J=15.3, 7.8 Hz, 0.5H), 4.49–4.38 (m, 2H), 4.25–4.15 (m, 1H), 3.99–3.76 (m, 1H), 3.71–3.60 (m, 2H), 3.43 (s, 3H), 3.35–3.23 and 3.10–2.41 (m, 8H), 2.36–2.14 (m, 4H), 2.00–1.60 (m, 6H), 1.36 and 1.28 (d, J=7.0 Hz, 3H).

EXAMPLE 1(4)

(11α, 15α, 13E)-9-oxo-11,15-Dihydroxy-16-(3-methoxymethylphenyl)-2,3-propano-17,18,19,20-tetranor-5-thiaprost-13-en-1-alcohol

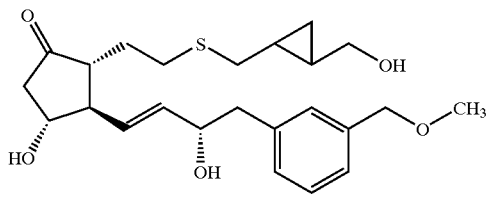

TLC: Rf 0.22 (ethyl acetate:methanol=20:1); NMR (CDCl$_3$): δ 7.38–7.10 (m, 4H), 5.75 (dd, J=15.3, 6.0 Hz, 1H), 5.53 (dd, J=15.3, 8.0 Hz, 1H), 4.48–4.38 (m, 3H), 4.00–3.89 (m, 1H), 3.63–3.53 (m, 1H), 3.46–3.17 (m, 5H), 2.95–2.14 (m, 11H), 1.99–1.62 (m, 3H), 1.06–0.84 (m, 2H), 0.58–0.44 (m, 2H).

Formulation Example 1

The following compounds were admixed in conventional method and punched out to obtain 100 tablets each containing 0.5 mg of active ingredient.

| | |
|---|---|
| (11α,15α,13E)-9-oxo-11,15-dihydroxy-16-(3-methoxy-methylphenyl)-17,18,19,20-tetranor-5-thiaprost-13-en-1-alcohol · α-cyclodextrin | 250 mg (active ingredient 50 mg) |
| Carboxymethylcellulose calcium | 200 mg |
| Magnesium stearate | 100 mg |
| Micro crystalline cellulose | 9.2 g |

Formulation Example 2

The following components were admixed in a conventional method, and the solution was sterilized in a conventional method, placed 1 ml portions into ampoules and freeze-dried in a conventional method to obtain 100 ampoules each containing 0.2 mg of active ingredient.

| | |
|---|---|
| (11 α,15 α,13E)-9-oxo-11,15-dihydroxy-16-(3-methoxy-methylphenyl)-17,18,19,20-tetranor-5-thiaprost-13-en-1-alcohol · α-cyclodextrin | 100 mg (active ingredient 20 mg) |
| Mannit | 5 g |
| Distilled water | 100 ml |

What is claimed is:

1. A 5-thia-ω-substituted phenyl-prostaglandin E alcohol of the formula (I)

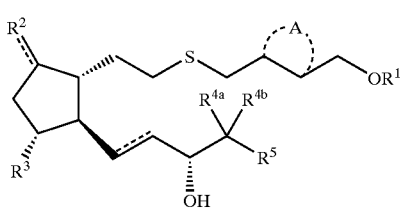

(wherein, —A— is absent or —A— is methylene or ethylene, $R^1$ is hydrogen, C1–6 alkyl, phenyl-C1–6 alkyl, C2–6 alkanoyl, or phenyl-C2–6 alkanoyl, $R^2$ is oxo or halogen, $R^3$ is hydrogen or hydroxy, $R^{4a}$ and $R^{4b}$ are, independently, hydrogen or C1–4 alkyl, $R^5$ is phenyl substituted with the following group:
  i) 1–3 of group selected from the group consisting of
    C1–4 alkyloxy-C1–4 alkyl,
    C2–4 alkenyloxy-C1–4 alkyl,
    C2–4 alkynyloxy-C1–4 alkyl,
    C3–7 cycloalkyloxy-C1–4 alkyl,
    C3–7 cydoalkyl(C1–4 alkyloxy)-C1–4 alkyl,
    phenyloxy-C1–4 alkyl,
    phenyl-C1–4 alkyloxy-C1–4 alkyl,
    C1–4 alkylthio-C1–4 alkyl,
    C2–4 alkenylthio-C1–4 alkyl,
    C2–4 alkynylthio-C1–4 alkyl,
    C3–7 cycloalkylthio-C1–4 alkyl,
    C3–7 cycloalkyl(C1–4 alkylthio-)-C1–4 alkyl,
    phenylthio-C1–4 alkyl, and
    phenyl-C1–4 alkylthio-C1–4 alkyl,
  ii) C1–4 alkyloxy-C1–4 alkyl and C1–4 alkyl,
    C1–4 alkyloxy-C1–4 alkyl and C1–4 alkyloxy,
    C1–4 alkyloxy-C1–4 alkyl and hydroxy,
    C1–4 alkyloxy-C1–4 alkyl and halogen,
    C1–4 alkylthio-C1–4 alkyl and C1–4 alkyl,
    C1–4 alkylthio-C1–4 alkyl and C1–4 alkyloxy,
    C1–4 alkylthio-C1–4 alkyl and hydroxy, or
    C1–4 alkylthio-C1–4 alkyl and halogen,
  iii) haloalkyl or hydroxy-C1–4 alkyl, or
  iv) C1–4 alkyl and hydroxy;
  ═══ is a single bond or a double bond)
or cyclodextrin clathrate thereof.

2. The compound according to claim 1, wherein $R^2$ is oxo.

3. The compound according to claim 1, wherein $R^2$ is halogen.

4. The compound according to claim 1, wherein $R^3$ is hydrogen.

5. The compound according to claim 1, wherein $R^3$ is hydroxy.

6. The compound according to claim 1, wherein $R^5$ is phenyl substituted with
  i) 1–3 of substituent(s) selected from
    C1–4 alkyloxy-C1–4 alkyl,
    C2–4 alkenyloxy-C1–4 alkyl,
    C2–4 alkynyloxy-C1–4 alkyl,
    C3–7 cycloalkyloxy-C1–4 alkyl,
    C3–7 cycloalkyl(C1–4 alkyloxy)-C1–4 alkyl,
    phenyloxy-C1–4 alkyl,
    phenyl-C1–4 alkyloxy-C1–4 alkyl,
    C1–4 alkylthio-C1–4 alkyl,
    C2–4 alkenylthio-C1–4 alkyl,
    C2–4 alkynylthio-C1–4 alkyl,
    C3–7 cycloalkylthio-C1–4 alkyl,
    C3–7 cycloalkyl (C1–4 alkylthio-)-C1–4 alkyl,
    phenylthio-C1–4 alkyl, or
    phenyl-C1–4 alkylthio-C1–4 alkyl.

7. The compound according to claim 1, wherein $R^5$ is phenyl substituted with
  ii) C1–4 alkyloxy-C1–4 alkyl and C1–4 alkyl,
    C1–4 alkyloxy-C1–4 alkyl and C1–4 alkyloxy,
    C1–4 alkyloxy-C1–4 alkyl and hydroxy,
    C1–4 alkyloxy-C1–4 alkyl and halogen,
    C1–4 alkylthio-C1–4 alkyl and C1–4 alkyl,
    C1–4 alkylthio-C1–4 alkyl and C1–4 alkyloxy,
    C1–4 alkylthio-C1–4 alkyl and hydroxy, or
    C1–4 alkylthio-C1–4 alkyl and halogen.

8. The compound according to claim 1, wherein $R^5$ is phenyl substituted with iii) haloalkyl, or hydroxy-C1–4 alkyl.

9. The compound according to claim 1, wherein $R^5$ is phenyl substituted with iv) C1–4 alkyl and hydroxy.

10. The compound according to claim 1, which is
  (15α, 13E)-9-oxo-15-hydroxy-16-(3-methoxymethylphenyl)-17,18,19,20-tetranor-5-thiaprost-13-en-1-alcohol,
  (11α, 15α, 13E)-9-oxo-11,15-dihydroxy-16-(3-methoxymethylphenyl)-17,18,19,20-tetranor-5-thiaprost-13-en-1-alcohol,
  (11α, 15α, 13E)-9-oxo-11,15-dihydroxy-16-methyl-16-(3-methyl-4-hydroxyphenyl)-17,18,19,20-tetranor-5-thiaprost-13-en-1-alcohol,
  (11α, 15α, 13E)-9-oxo-11,15-dihydroxy-16-methyl-16-(3-methoxymethylphenyl)-17,18,19,20-tetranor-5-thiaprost-13-en-1-alcohol, or
  (11α, 15α, 13E)-9-oxo-11,15-dihydroxy-16-(3-methoxymethylphenyl)-2,3-propano-17,18,19,20-tetranor-5-thiaprost-13-en-1-alcohol.

11. A process which comprises reacting a compound of the formula (II)

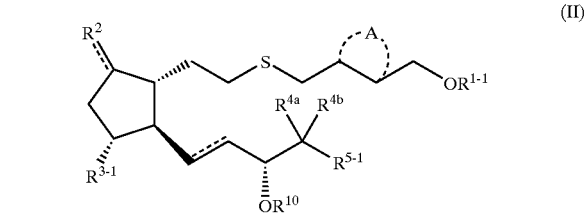

(wherein, $R^{1-1}$ is C1–6 alkyl, phenyl-C1–6 alkyl, C2–6 alkanoyl, phenyl-C2–6 alkanoyl,
or a protecting group of hydroxy which is removed under an acidic condition, $R^{3-1}$ is hydrogen, or hydroxy protected by a protecting group of hydroxy which is removed under an acidic condition, $R^{10}$ is a protecting group of hydroxy which is removed under an acidic condition, $R^{5-1}$ is the same meaning of $R^5$ in claim 1 provided that a hydroxy in the group represented by $R^{5-1}$ is protected by a protecting group of hydroxy which is removed under an acidic condition, and the other symbols are the same meaning as defined hereinbefore)

for removal of a protecting group under an acidic condition to obtain a compound of the formula (I)

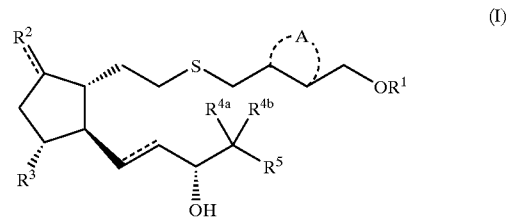

(wherein, all the symbols are the same meaning as defined in claim 1).

12. A pharmaceutical composition comprising a 5-thia-ω-substituted phenyl-prostaglandin E alcohol of the formula (I) according to claim 1, or cyclodextrin clathrate thereof as an active ingredient.

* * * * *